(12) United States Patent
Kahre et al.

(10) Patent No.: US 6,555,101 B1
(45) Date of Patent: *Apr. 29, 2003

(54) HAIR AFTERTREATMENT PREPARATIONS

(75) Inventors: Joerg Kahre, Monheim (DE); Hermann Hensen, Haan (DE); Thomas Mueller-Kirschbaum, Solingen (DE); Dagmar Goebels, Duesseldorf (DE); Holger Tesmann, Juechen (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/433,198

(22) Filed: Nov. 3, 1999

Related U.S. Application Data

(63) Continuation of application No. 08/703,576, filed on Aug. 2, 1996, now Pat. No. 6,056,947.

(30) Foreign Application Priority Data

| Sep. 29, 1992 | (DE) | 42 32 506 |
| Sep. 29, 1992 | (DE) | 42 32 512 |
| Oct. 13, 1992 | (DE) | 42 34 413 |
| Oct. 13, 1992 | (DE) | 42 34 405 |
| May 27, 1993 | (DE) | 43 17 576 |

(51) Int. Cl.$^7$ .............................................. A61K 7/075
(52) U.S. Cl. ...................................................... 424/70.1
(58) Field of Search ..................................... 424/70.19

(56) References Cited

U.S. PATENT DOCUMENTS 6,056,947 A * 5/2000 Kahre et al. ............. 424/70.13

FOREIGN PATENT DOCUMENTS

| DE | WO 91/03229 | * 3/1991 | 424/70.13 |
| WO | 91/03229 | * 3/1991 | |

* cited by examiner

Primary Examiner—Russell Travers
Assistant Examiner—Alysia Berman
(74) Attorney, Agent, or Firm—John E. Drach; Steven J. Trzaska

(57) ABSTRACT

A process for treating washed hair to provide hair with improved combability, comprising contacting hair with a water based composition comprising 0.1–3% by weight of a zwitterionic polymer; 0.01–10% by weight of an alkylpolyglycoside; 0.5–20% by weight of a fatty alcohol and the balance water.

7 Claims, No Drawings

HAIR AFTERTREATMENT PREPARATIONS

This application is a continuation of U.S. application Ser. No. 08/703,576, filed Aug. 2, 1996 now U.S. Pat. No. 6,056,947 and claims priority to German applications 42 32 512.9 and 42 32 506.4, filed Sep. 29, 1992, 42 34 405.0 and 42 34 413.1, filed Oct. 13, 1992 and 43 17596.7, filed May 27, 1993.

BACKGROUND OF THE INVENTION

This invention relates to the use of preparations containing special combinations of active substances for the cleaning and care of keratin fibers, more particularly hair.

The washing and care of hair is an important part of personal hygiene. Both the washing and care of hair, for example with shampoos, and the decorative finishing of hair styles, for example by coloring or permanent waving, are measures which affect the natural structure and properties of hair. For example, the wet and dry combability of hair, its hold and its body can be unsatisfactory following such a treatment. In addition, the hair can have an increased number of split ends or can "fly" as a result of electrostatic charging.

Accordingly, it has long been standard practice to subject the hair to a special aftertreatment. To this end, the hair is treated, normally by rinsing, with special active substances, for example quaternary ammonium salts or special polymers. Combability, hold and body are improved and the number of split ends is reduced by this treatment, depending on the formulation used. In addition, increased efforts have recently been made to find active substances or combinations of active substances which could be directly incorporated in various hair treatment preparations and which would thus eliminate the need for the additional aftertreatment step.

Additions of cationic polymers to hair treatment preparations generally lead to an improvement in wet and dry combability. Additions of amphoteric polymers produce significant improvements in wet combability, but generally have little effect on dry combability.

Whereas the improvement in wet combability, i.e. a reduction in wet combing work, is desirable in every case, the circumstances regarding dry combability are more complicated. Low combing work values characterize an improvement in combability. However, if combing work is overly reduced, the hair loses body and hold so that, in extreme cases, certain styles can no longer be created. Accordingly, a certain increase in dry combing work may be entirely desirable, above all in the case of relatively intricate styles, in order to improve style retention. In many cases, however, this involves increased electrostatic charging of the hair which leads to the unwanted phenomenon of "flying" of the hair.

Accordingly, there is still a need for improved active substances and combinations of active substances for the aftertreatment of hair or for incorporation in known hair-washing and hair-care preparations.

DESCRIPTION OF THE INVENTION

It has now surprisingly been found that active-substance combinations of certain polymers (A), special alkyl polyglycosides (B) and fatty compounds or waxes (C) can make a considerable contribution towards solving this problem. The hair treated with such combinations shows very good wet combability while its dry combability is in a very favorable range for style retention without electrostatic charging and hence "flying" of the hair being observed to any significant extent.

Accordingly, the present invention relates to the use of a water-based preparation which is characterized by a content of a) polymers (A) selected from the group of cationic, amphoteric, zwitterionic and nonionic polymers,
b) alkyl polyglycosides (B) corresponding to general formula (I):

$$RO-(Z)_x \qquad (I)$$

in which
R is an alkyl radical containing 6 to 22 carbon atoms,
Z is a mono- or oligosaccharide,
x is a number of 1.1 to 5,
or adducts thereof with 1 to 10 molecules of ethylene oxide and/or propylene oxide and
c) fatty compounds and/or waxes (C)
for the washing and care of keratin fibers, more particularly human hair.

All three classes of active substance are well-known constituents of hair treatment preparations.

Combinations of two of these three classes of active substance are also known. Thus, a shampoo containing a glucoside alkyl ether (Triton CG 110) and polyethoxylated lauryl alcohol in addition to a cationic polymer (Gafquat 755) is known from an Example of DE-OS 32 16 687. Combinations of cationic polymers and alkyl saccharides are also known from EP-A1-337 354.

Finally, combinations of alkyl glycosides, cationic or zwitterionic polymers and fatty alcohols or mono- and triglycerides in permanent wave formulations are known from Examples of hitherto unpublished German applications P 42 32 512.9, P 42 32 506.4, P 42 34 413.1 and P 42 34 405.0. Corresponding combinations for shampoos and tinting shampoos are known from Examples of P 42 32 506.4.

However, there are no indications in this prior art of the advantageous effects obtained by using the three-component combination of active substances according to the invention in preparations for the washing and care of keratin fibers, more particularly hair. In the context of the invention, "hair-care preparations" are only understood to be preparations which help to (re)establish natural properties of hair, such as good combability, style retention, body, etc. This expression specifically does not include permanent wave preparations, hair dyes, tinting shampoos and hair setting preparations which alter the appearance of the hair for decorative purposes.

The preparations used in accordance with the invention preferably contain 0.1 to 3% by weight of polymers (A), 0.01 to 10% by weight of alkyl polyglycosides (B) and 0.5 to 20% by weight of fatty compounds or waxes (C), based on the preparation as a whole.

The first component of the active-substance combination according to the invention is selected from the group of cationic, amphoteric, zwitterionic and nonionic polymers.

The cationic polymers suitable for use in accordance with the invention contain cationic groups within the polymer skeleton. These groups may be part of the polymer chain, although they may also be positioned inside chains which are attached to a main chain by intermediate members. Typical cationic groups contain quaternary nitrogen or phosphorus atoms. Groups containing quaternary nitrogen atoms are preferred. The quaternary nitrogen atoms may carry four different substituents or partly the same substituents and may also be part of a ring system. Preferred cationic groups are ammonium and imidazolinium groups.

If the ionic groups are situated in the side chains, the polymers are synthesized from compounds which, in addition to at least one cationic group, contain at least one polymerizable group and are free from anionic groups.

The polymerizable group is preferably a vinyl group. However, cationic polymers in which the main polymer chain is made up, for example, of glycosides or is protein-like in character may also be used.

Cationic copolymers containing at least one nonionic monomer in addition to the cationic monomers are also preferred for the purposes of the invention. Suitable nonionic monomers are, for example, vinyl pyrrolidone, vinyl, acetate, acrylamide, methacrylamide, methyl acrylate, ethyl acrylate, methyl methacrylate and ethyl methacrylate. Vinyl pyrrolidone is a particularly preferred nonionic monomer.

Several cationic polymers suitable for hair-care purposes are known to the expert and are available as commercial products.

Examples of such polymers are:

Quaternized cellulose derivatives of the type commercially available as Celquat® and Polymer JR®. The compounds Celquat H 100, Celquat L 200 and Polymer JR®400 are preferred quaternized cellulose derivatives.

Quaternized guar derivatives of the type commercially available as Cosmedia Guar® and Jaguar®. Preferred guar derivatives are, for example, Cosmedia Guar® C-261 and Jaguars C 13-S.

Copolymers of vinyl pyrrolidone with quaternized derivatives of dialkyl aminoacrylate and methacrylate, such as for example vinyl pyrrolidone/dimethyl aminomethacrylate copolymers quaternized with diethyl sulfate. Compounds such as these are commercially available as Gafquat®734 and Gafquat®755.

Copolymers of vinyl pyrrolidone with vinyl imidazolinium methochloride of the type commercially available as Luviquat®.

Polymeric dimethyl diallyl ammonium salts and copolymers thereof with esters and amides of acrylic acid and methacrylic acid. The polymers commercially available as Merquat®100 (poly(dimethyl diallyl ammonium chloride)) and Merquat®550 (dimethyl diallyl ammonium chloride/acrylamide copolymer) are examples of such cationic polymers.

Cationically derivatized protein hydrolyzates obtainable, for example, by reaction of alkali-, acid- or enzyme-hydrolyzed proteins with glycidyl trialkyl ammonium salts or 3-halo-2-hydroxypropyl trialkyl ammonium salts. The proteins, which may serve as starting materials for the protein hydrolyzates, may be of both animal and vegetable origin. Typical starting materials are, for example, keratin, collagen, elastin, soya protein, milk protein, wheat protein, silk protein and almond protein. The hydrolysis results in the formation of mixtures with molecular weights of around 100 to around 50,000 dalton. Typical average molecular weights are in the range from about 500 to about 5,000 dalton. Further particulars of cationic derivatization can be found inter alia in Japanese patent application 77/73485 (Chemical Abstracts, abstract 90:174508v).

The cationically derivatized protein hydrolyzates advantageously contain one or two long alkyl chains containing 8 to 22 carbon atoms and, accordingly, two or one short alkyl chain containing 1 to 4 carbon atoms. Compounds containing one long alkyl chain are preferred.

Preferred compounds (A) correspond to formula (IV):

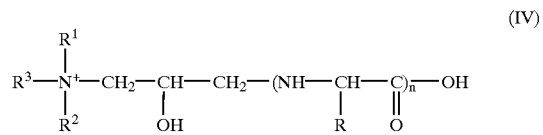

(IV)

in which R stands for the side chains of the amino acids of the protein, $R^1$ and $R^2$ independently of one another are alkyl chains containing 1 to 4 carbon atoms and $R^3$ is an alkyl chain containing 8 to 22 carbon atoms.

A commercially available product is Lamequat®L (a product of Chemische Fabrik Grünau). It has the following structure:

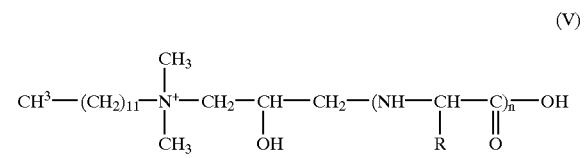

(V)

in which R stands for the side chains of the amino acids of collagen. A CTFA-analogous name is Lauryl-dimonium Hydroxypropylamino Hydrolyzed Collagene.

Polymeric condensation resins of polyols and polyamines such as, for example, polyglycol/polyamine condensation resins of the type known by the CTFA name of PEG-15 Cocopolyamine. The product Polyquart®H 81 (Henkel), for example, is commercially available.

In the context of the present invention, "amphoteric polymers" are understood to be polymers which contain both free amino groups and free —COOH— or —SO$_3$H- groups in the molecule and which are capable of forming inner salts. "Zwitterionic polymers" are understood to be polymers which contain quaternary ammonium groups and —COO⁻— or —SO$_3$⁻-groups in the molecule.

Examples of amphoteric polymers suitable for use in accordance with the invention are the acrylic resins commercially available as Amphomer® and Amphomer® LV-71, copolymers of tert.-butyl aminoethyl methacrylate, N-(1,1,3,3-tetramethylbutyl)-acrylamide and two or more monomers from the group comprising acrylic acid, methacrylic and simple esters thereof.

Other amphoteric or zwitterionic polymers suitable for use in accordance with the invention are the compounds mentioned in GB-A-2,104,091, EP-A-47 714, EP-A-217 274, EP-A-283 817 and DE-A-28 17 369.

Particularly preferred zwitterionic polymers are those which are essentially made up of (α) monomers containing quaternary ammonium groups corresponding to general formula (I):

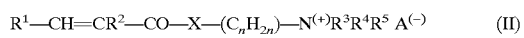

(II)

in which $R^1$ and $R^2$ independently of one another represent hydrogen or a methyl group and $R^3$, $R^4$ and $R^5$ independently of one another represent alkyl groups containing 1 to 4 carbon atoms, X is an NH group or an oxygen atom, n is an integer of 2 to 5 and $A^{(-)}$ is the anion of an organic or inorganic acid and (β) monomeric carboxylic acids corresponding to general formula (II):

(III)

in which $R^6$ and $R^7$ independently of one another represent hydrogen or methyl groups.

These compounds may be used in accordance with the invention both directly and in the salt form obtained by neutralization of the polymers, for example with an alkali metal hydroxide. Particulars of the production of these polymers can be found in DE-A-39 29 973.

Polymers based on monomers of the ($\alpha$) type, in which $R^3$, $R^4$ and $R^5$ are methyl groups, X is an NH group and $A^{(-)}$ is a halide, methoxysulfate or ethoxysulfate ion, are most particularly preferred. Acrylamidopropyl trimethyl ammonium chloride and methacrylamidopropyl trimethyl ammonium chloride are particularly preferred monomers ($\alpha$). Acrylic acid or an alkali metal salt of acrylic acid, more particularly the sodium salt, is preferably used as the monomer ($\beta$) for the polymers mentioned.

Zwitterionic polymers in which the number of monomers of the ($\alpha$) type is greater than the number of monomers of the ($\beta$) type are also preferred. Ratios of ($\alpha$) monomers to ($\beta$) monomers of greater than 1.5 are particularly preferred.

Other preferred zwitterionic polymers are polysiloxane/polyorganobetaine copolymers.

Suitable nonionic polymers are, for example, polyvinyl pyrrolidones, for example the products commercially available as Luviskol® K 30 and Luviskol® K 90 (BASF).

Vinyl pyrrolidone/vinyl acetate copolymers of the type marketed, for example, as Luviskol® (BASF). Luviskol® VA 64, Luviskol® VA 73 and Luviskol® VA 37 are preferred nonionic polymers; Luviskol® VA 37 is particularly preferred.

Vinyl pyrrolidone/dimethylaminoethyl methacrylate/vinyl caprolactam terpolymers of the type commercially available, for example, as Copolymer VC-713 (GAF).

Among the polymers (A), amphoteric and zwitterionic polymers are preferred. Zwitterionic polymers made up of at least one cationic monomer and at least one anionic monomer have proved to be most particularly suitable for the purposes of the invention.

The second component of the active-substance combination according to the invention consists of alkyl polyglycosides corresponding to formula (I).

The compounds corresponding to formula (I) are characterized by the following parameters.

The alkyl radical R contains 6 to 22 carbon atoms and may be both linear and branched. Preferred alkyl radicals are primary linear and 2-methyl-branched aliphatic radicals. Alkyl radicals such as these are, for example, 1-octyl, 1-decyl, 1-lauryl, 1-myristyl, 1-cetyl and 1-stearyl. 1-octyl, 1-decyl, 1-lauryl and 1-myristyl are particularly preferred. Where so-called "oxoalcohols" are used as starting materials, compounds with an odd number of carbon atoms in the alkyl chain predominate.

The alkyl glycosides suitable for use in accordance with the invention may contain only one particular alkyl radical R. However, these compounds are normally prepared from natural fats and oils or mineral oils. In this case, mixtures corresponding to the starting compounds or to the particular working-up of these compounds are present as the alkyl radicals R.

Particularly preferred alkyl polyglycosides are those in which R consists essentially of $C_8$ and $C_{10}$ alkyl groups,
essentially of $C_{12}$ and $C_{14}$ alkyl groups,
essentially of $C_8$ and $C_{16}$ alkyl groups, or
essentially of $C_{12}$ and $C_{16}$ alkyl groups.

Any mono- or oligosaccharides may be used as the sugar unit Z. Sugars containing 5 or 6 carbon atoms and the corresponding oligosaccharides are normally used. Sugars such as these are, for example, glucose, fructose, galactose, arabinose, ribose, xylose, lyxose, allose, altrose, mannose, gulose, idose, talose and sucrose. Preferred sugar units are glucose, fructose, galactose, arabinose and sucrose; glucose is particularly preferred.

The alkyl polyglycosides suitable for use in accordance with the invention contain on average 1.1 to 5 sugar units. Alkyl glycosides with values for x of 1.3 to 2 are particularly preferred. Alkyl glycosides in which x=1.4 to 1.6 are most particularly preferred.

The alkoxylated homologs of the alkyl polyglycosides mentioned may also be used in accordance with the invention. These homologs may contain on average up to 10 ethylene oxide and/or propylene oxide units per alkyl glycoside unit. These compounds also are not normally individual compounds, but have a corresponding homolog distribution according to the ethoxylation process used. Alkoxylated compounds of the type in question may be obtained, for example, by using ethoxylated fatty alcohols for the synthesis of the alkyl polyglycosides.

It has surprisingly been found that even comparatively small quantities of component (B) are sufficient to obtain the effects according to the invention. Accordingly, it may be preferable to use component (B) in quantities of only 0.1 to 0.9% by weight, based on the preparation as a whole.

The third component of the active-substance combination according to the invention are fatty compounds and waxes.

Preferred fatty compounds are fatty alcohols. Saturated and unsaturated, linear and branched fatty alcohols containing 8 to 24 carbon atoms are particularly preferred. Preferred fatty alcohols include decyl alcohol, lauryl alcohol, myristyl alcohol, cetyl alcohol, stearyl alcohol, oleyl alcohol, isostearyl alcohol and hydroxystearyl alcohol.

Other preferred fatty compounds are mono-, di- and triglycerides, i.e. the mono-, di- and triesters of glycerol with fatty acids, such as for example lauric acid, myristic acid, palmitic acid, stearic acid, isostearic acid, oleic acid, linoleic acid, linolenic acid, erucic acid, hydroxystearic acid and ricinoleic acid. The diesters and triesters may be both esters containing only one type of fatty acid and esters containing various fatty acids. Particularly preferred glycerides are glycerol monostearate and distearate, glycerol monooleate and glycerol monoisostearate and diisostearate.

Spermaceti, beeswax, montan wax and paraffins are waxes which may be used in accordance with the invention as component (C).

In addition to the active-substance combination according to the invention, the preparations suitable for use in accordance with the invention may contain any of the constituents typically encountered in such preparations. If the preparations according to the invention are hair-washing preparations, they normally contain surface-active compounds. Depending on the formulation, the preparations may contain anionic, zwitterionic, ampholytic, cationic or nonionic surfactants.

Anionic surfactants suitable for the hair-treatment preparations according to the invention are any of the anionic surfactants which are suitable for use on the human body. They are characterized by a water-solubilizing anionic group, for example a carboxylate, sulfate, sulfonate or phosphate group, and a lipophilic alkyl group containing approximately 10 to 22 carbon atoms. Glycol or polyglycol ether groups, ester, ether and amide groups and also hydroxyl groups may also be present in the molecule. The following are examples of suitable anionic surfactants in the form of the sodium, potassium and ammonium salts and also the mono-, di- and trialkanolammonium salts containing 2 or 3 carbon atoms in the alkanol group:

linear fatty acids containing 10 to 22 carbon atoms (soaps), ether carboxylic acids corresponding to the formula R—O—(CH$_2$—CH$_2$O)$_x$—CH$_2$—COOH, in which R is a linear alkyl group containing 10 to 22 carbon atoms and x=0 or 1 to 10, acyl sarcosides containing 10 to 18 carbon atoms in the acyl group, acyl taurides containing 10 to 18 carbon atoms in the acyl group, acyl isethionates containing 10 to 18 carbon atoms in the acyl group, sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups, linear alkane sulfonates containing 12 to 18 carbon atoms, linear alpha-olefin sulfonates containing 12 to 18 carbon atoms, alpha-sulfofatty acid methyl esters of fatty acids containing 12 to 18 carbon atoms, alkyl sulfates and alkyl polyglycol ether sulfates corresponding to the formula R—O(CH$_2$—CH$_2$O)$_x$—OSO$_3$H, in which R is a preferably linear alkyl group containing 10 to 18 carbon atoms and x=0 or 1 to 12, mixtures of surface-active hydroxysulfonates according to DE-A-37 25 030, sulfated hydroxyalkyl polyethylene and/or hydroxyalkylene propylene glycol ethers according to DE-A-37 23 354, sulfonates of unsaturated fatty acids containing 12 to 24 carbon atoms and 1 to 6 double bonds according to DE-A-39 26 344, esters of tartaric acid and citric acid with alcohols which are adducts of approximately 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and also sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups.

Zwitterionic surfactants are surface-active compounds which contain at least one quaternary ammonium group and at least one —COO$^{(-)}$ or —SO$_3^{(-)}$ group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacyl aminopropyl dimethyl ammonium glycinate, and 2-alkyl-3-carboxymethyl-3-hydroxyethyl imidazolines containing 8 to 18 carbon atoms in the alkyl or acyl group and cocoacyl aminoethyl hydroxyethyl carboxymethyl glycinate. A preferred zwitterionic surfactant is the fatty acid amide derivative known by the CTFA name of Cocamidopropyl Betaine.

Ampholytic surfactants are surface-active compounds which, in addition to a C$_{8-18}$ alkyl or acyl group in the molecule, contain at least one free amino group and at least one —COOH or —SO$_3$H group and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids all containing approximately 8 to 18 carbon atoms in the alkyl group. Particularly preferred ampholytic surfactants are N-cocoalkyl aminopropionate, cocoacyl aminoethyl aminopropionate and C$_{12-18}$ acyl sarcosine.

Suitable cationic surfactants for the hair treatment preparations according to the invention are, in particular, quaternary ammonium compounds, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other suitable cationic surfactants are so-called esterquats (for example Stepantex® VS 90, Dehyquart® AU 36 and AU 56) and amidoamines (for example Tegoamid® S 18).

Nonionic surfactants contain, for example, a polyol group, a polyalkylene glycol ether group or a combination of polyol and polyglycol ether groups as the hydrophilic group. Examples of compounds such as these are adducts of 2 to 30 moles of ethylene oxide and/or 0 to 5 moles of propylene oxide with linear fatty alcohols containing 8 to 22 carbon atoms, with fatty acids containing 12 to 22 carbon atoms and with alkylphenols containing 8 to 15 carbon atoms in the alkyl group, C$_{12-22}$ fatty acid monoesters and diesters of adducts of 1 to 30 moles of ethylene oxide with glycerol, glycerol mono- and diesters and sorbitan mono- and diesters of saturated and unsaturated C$_{8-22}$ fatty acids and ethylene oxide adducts thereof and adducts of 5 to 60 moles of ethylene oxide with castor oil and hydrogenated castor oil.

The compounds containing alkyl groups used as surfactants may be individual substances. However, it is generally preferred to produce the compounds in question from native vegetable or animal raw materials so that mixtures of compounds differing in their alkyl chain lengths according to the particular raw material used are obtained.

The surfactants which are adducts of ethylene and/or propylene oxide with fatty alcohols or derivatives of such adducts may be both products having a "normal-range" homolog distribution and also products having a "narrow-range" homolog distribution. "Normal-range" products are mixtures of homologs which are obtained in the reaction of fatty alcohol and alkylene oxide using alkali metals, alkali metal hydroxides or alkali metal alcoholates as catalysts. By contrast, narrow-range products are obtained when, for example, hydrotalcites, alkaline earth metal salts of ether carboxylic acids, alkaline earth metal oxides, hydroxides or alcoholates are used as catalysts. It may be preferable to use narrow-range products, particularly where they are ethoxylated fatty alcohols which also act as thickeners.

The preparations according to the invention preferably contain the surface-active compounds A in quantities of 0.5 to 20% by weight, based on the particular preparation.

The active-substance combinations according to the invention are used with particular preference in hair aftertreatment preparations, i.e. preparations which are used after washing of the hair or any other treatment of the hair, such as permanent waving or dyeing. With preparations such as these, it may be preferable to formulate them without ionic, more particularly cationic and anionic, surfactants.

Other typical constituents of the preparations used in accordance with the invention may be:
- thickeners, such as agar agar, guar gum, alginates and xanthan gum or esters of ethoxylated polyols and fatty acids, such as for example polyglyceryl(2)-polyoxyethylene(4) stearate,
- structurants, such as glucose and maleic acid,
- protein hydrolyzates, more particularly elastin, collagen, keratin, milk protein, soya protein, almond and wheat protein hydrolyzates and condensation products thereof with fatty acids,
- perfume oils, dimethyl isosorbide and cyclodextrins,
- solubilizers, such as ethanol, isopropanol, ethylene glycol, propylene glycol, glycerol and diethylene glycol and ethoxylated fatty alcohols,
- dyes,
- antidandruff agents, such as Piroctone Olamine and Zink Omadine,
- pH regulators, such as citric acid/sodium citrate buffer,
- active substances, such as panthenol, allantoin, pyrrolidone carboxylic acids, plant extracts and vitamins,
- light stabilizers,
- consistency regulators, such as sugar esters, polyol esters or polyol alkyl ethers,
- superfatting agents, such as polyethoxylated lanolin derivatives, lecithin derivatives and fatty acid alkanolamides,
- complexing agents, such as EDTA, NTA and phosphonic acids,
- swelling and penetration agents, such as glycerol, propylene glycol monoethyl ether, carbonates, hydrogen carbonates, guanidines, ureas and primary, secondary and tertiary phosphates,
- metal soaps, such as for example zinc or aluminium stearate,
- opacifiers, such as latex,
- pearlescers, such as ethylene glycol monostearate and distearate,
- propellents, such as propane/butane mixtures, $N_2O$, dimethyl ether and air and
- antioxidants.

The preparations suitable for use in accordance with the invention can be formulated as lotions, emulsions, microemulsions, solutions, creams or gels. They are preferably formulated as lotions, emulsions or microemulsions with a water content of 50 to 90% by weight, based on the preparation as a whole. Narrow-range ethoxylated fatty alcohols and esters of ethoxylated polyols and fatty acids and, optionally even metal soaps are preferably used for establishing the required viscosity of the formulation.

In another preferred embodiment, the preparations may be formulated as foam aerosols which are packed in aerosol containers with a foam valve together with a liquefied gas, such as for example propane/butane mixtures, nitrogen, $CO_2$, air, $N_2O$, dimethyl ether, fluorocarbon and chlorinated hydrocarbon propellents or mixtures thereof.

EXAMPLES

I. Determination of Wet and Dry Combability and Electrostatic Charging

Test methods

The combability tests were carried out by the method according to J. Soc. Cosm. Chem. 1973 [24] 782.

Combing work was studied on brown hair (Alkinco #6634, tress length 12 cm, tress weight 1 g). The hair used was lightly predamaged ("medium-bleached") hair which the average consumer would be expected to have. The hairs are treated for 30 minutes with a 6% $H_2O_2$ solution which was adjusted with ammonia to a pH value of 9.4. After the zero measurement, the tresses were soaked with 1 g of the composition to be tested per g of hair. After a contact time of 5 minutes, the tresses were rinsed out for 1 minute in running water (1 l/min., 38° C.). To determine wet combing work, the tresses were then remeasured. To determine dry combing work, the tresses were first dried for 12 hours at 30° C./20% relative air humidity and then measured.

Dry combing work was measured in the presence of electrostatic charging which was determined at the same time as the dry combing work. Electrostatic charging was measured via the charge tap of a double Faraday cage after 10 combings.

Results:

The composition of the mixtures tested and the results of the measurements are set out in Table 1. The results represent the average value of 20 measurements with 20 different tresses and are based on the value of the zero measurement. They had a statistical certainty of 99.0 or 99.99%.

TABLE 1

[Quantities in parts by weight]

| Component/Mixture | C1 | I1 | C2 | I2 |
|---|---|---|---|---|
| Cetyl/stearyl alcohol (1:1) | 3.2 | 3.2 | 3.2 | 3.2 |
| Plantaren ®1200[1] | — | 1.0 | — | 1.0 |
| Polyquart ®H 81[2] | 2.0 | 2.0 | — | — |
| Acrylamidopropyl trimethyl ammonium chloride/acrylic acid (ratio by weight 70:30) co-polymer, neutralized with sodium hydroxide | — | — | 1.0 | 1.0 |
| Perfume oil | 0.1 | 0.1 | 0.1 | 0.1 |
| Cetyl/stearyl alcohol.20 EO | 0.8 | 0.8 | 0.8 | 0.8 |
| Water | ←ad 100→ | | | |
| Wet combing work [%] | 48 | 41 | 40 | 46 |
| Dry combing work [%] | 152 | 218 | 307 | 302 |
| Electrostatic charging [%] | 120 | 162 | 205 | 156 |

[1]$C_{12-16}$ alkyl polyglucoside (degree of polymerization 1.4; approx. 50% of active substance; CTFA name: Lauryl Polyglycose) (HENKEL CORP.)
[2]Polyglycol/polyamine condensation resin based on PEG epichlorohydrin/dipropylenetriamine/laurylamine(approx. 50% of active substance; CTFA name: PEG-15-Coco Polyamine) (HENKEL)

II. Formulation Examples

The quantities in the following Examples are % by weight.

1. Rinse

| | |
|---|---|
| Cetyl/stearyl alcohol | 3.2 |
| Plantaren ®2000[3] | 1.0 |
| Acrylamidopropyl trimethyl ammonium chloride/acrylic acid copolymer, neutralized with sodium hydroxide (P1 acc. to DE 39 29 973) | 1.0 |
| Perfume oil | 0.2 |
| cetyl/stearyl alcohol.20 EO | 1.2 |
| Sorbic acid | 0.4 |
| Water | ad 100 |

1. Rinse

[3]$C_{8-16}$ alkyl polyglucoside (degree of polymerization 1.4: approx. 50% of active substance; CTFA name: Decyl Polyglycose) (HENKEL)

2. Rinse

| | |
|---|---|
| Lanette ®16[4] | 3.2 |
| Plantaren ®2000 | 2.0 |
| Acrylamidopropyl trimethyl ammonium chloride/acrylic acid copolymer, neutralized with sodium hydroxide (P1 acc. to DE 39 29 973) | 1.0 |
| Cutina ® GMS[5] | 4.0 |
| Perfume oil | 0.1 |
| PHB ester | 0.3 |
| Water | ad 100 |

[4]Cetyl alcohol (CTFA name: Cetyl Alcohol) (HENKEL)
[5]Glycerol monostearate (CTFA name: Glyceryl Stearate) (HENKEL)

3. Rinse

| | |
|---|---|
| Lanette ®16 | 3.2 |
| Plantaren ®2000 | 2.0 |
| Cosmedia ® Guar C 261[6] | 1.0 |
| Perfume oil | 0.2 |
| Eumulgin ®HRE 40[7] | 0.3 |
| PHB ester | 0.2 |
| Water | ad 100 |

[6]Guar hydroxypropyl trimethyl ammonium chloride (90% of active substance; CTFA name: Guar Hydroxypropyl Trimonium Chloride) (HENKEL)
[7]Hydrogenated castor oil.40 EO (CTFA name: PEG-40 Hydrogenated Castor Oil) (HENKEL)

4. Shampoo

| | |
|---|---|
| Texapon ®N 28[8] | 35.0 |
| Lamepon ®S[9] | 9.0 |
| Plantaren ®1200 | 4.0 |
| Lanette ®14[10] | 1.5 |
| Cutina ®MD[11] | 0.5 |
| Merquat ®550[12] | 4.0 |
| Nutrilan ®I[13] | 1.0 |
| Glycerol | 0.5 |
| PHB ester | 0.3 |
| Vitamin E acetate | 0.3 |
| Water | ad 100 |

[8]Lauryl ether sulfate sodium salt (approx. 28% of active substance; CTFA name: Sodium Laureth Sulfate) (HENKEL)
[9]Protein hydrolyzate/fatty acid condensate potassium salt (CTFA name: Potassium Cocoyl Hydrolyzed Collagen) (HENKEL)
[10]Myristyl alcohol (CTFA name: Myristyl Alcohol) (HENKEL)
[11]Palmitic acid/stearic acid monoglyceride/diglyceride (CTFA name: Glyceryl Stearate) (HENKEL)
[12]Dimethyl diallyl ammonium chloride/acrylamide copolymer (8% of active substance in water; CTFA name: Polyquaternium 7) (MERCK & CO)
[13]Collagen hydrolyzate (approx. 39% of active substance; CTFA name: Hydrolyzed Collagen) (HENKEL)

5. Shampoo

| | |
|---|---|
| Texapon ®N 28 | 36.0 |
| Dehyton ®K[14] | 10.0 |
| Plantaren ®1200 | 3.0 |
| Lanette ®16 | 2.0 |
| Acrylamidopropyl trimethyl ammonium chloride/acrylic acid (70:30) copolymer, neutralized with sodium hydroxide | 1.0 |
| Luviskol ®K 30[15] | 0.3 |
| Perfume oil | 0.2 |
| Eumulgin ®HRE 40 | 0.5 |
| Gluadin ®Almond[18] | 0.5 |
| Water | ad 100 |

[14]Fatty acid amide derivative of betaine structure (approx. 30% of active substance; CTFA name: Cocoamidopropyl Betaine) (HENKEL)
[15]Polyvinyl pyrrolidone (95% of active substance; CTFA name: PVP) (BASF)
[16]Protein hydrolyzate of ground almond (22% of active substance; CTFA name: Hydrolyzed Almond Protein (HENKEL)

6. Mild shampoo

| | |
|---|---|
| Lamepon ®S | 20.0 |
| Plantaren ®2000 | 11.0 |
| Texapon ®SB3[17] | 5.0 |
| Dehyton ®K | 5.0 |
| Arlypon ®F[18] | 2.0 |
| Polymer JR ®-400[19] | 0.2 |
| Sodium chloride | 3.0 |
| Ethylene glycol distearate | 0.6 |
| Perfume oil | q.s. |
| Dye | q.s. |
| Water | ad 100.0 |

[17]Sulfosuccinic acid semiester based on an alkyl polyglycol ether, disodium salt (40% of active substance; CTFA name: Disodium Laurethsulfosuccinate) (HENKEL)
[18]$C_{12/14}$ fatty alcohol.2.5 EO (CTFA name: Laureth-2) (HENKEL)
[19]Quaternized hydroxyethyl cellulose (NATIONAL STARCH)

7. Cream care shampoo

| | |
|---|---|
| Cetyl/stearyl alcohol.20 EO | 1.0 |
| Octyl dodecanol | 2.0 |
| Lamecreme DGE 18[20] | 4.0 |
| Euperlan PK 3000[21] | 4.0 |
| Texapon ®N70[22] | 22.0 |
| Plantaren ®2000 | 16.0 |
| Lanette ®O[23] | 1.0 |
| Lamequat ®L | 1.0 |
| Water | ad 100.0 |

[20]Polyoxyethylene fatty acid polyglycerol ester (CTFA name: Polyglyceryl-2-PEG-4-Stearate) (HENKEL)
[21]Pearlescer concentrate containing ethylene glycol distearate (62% of active substance; CTFA name: Glycol Distearate (and) Glycerin (and) Laureth-4 (and) Cocoamidopropyl Betaine) (HENKEL)
[22]Sodium lauryl ether sulfate (72% of active substance; CTFA name: Sodium Laureth Sulfate) (HENKEL)
[23]Mixture of higher saturated alcohols (CTFA name: Cetearyl Alcohol) (HENKEL)

8. Shampoo

| | |
|---|---|
| Lamepon ®S | 26.0 |
| Plantaren ®1200 | 8.0 |
| Euperlan ®PK 3000 | 4.0 |
| Cetiol HE[24] | 2.0 |

-continued

| 8. Shampoo | |
|---|---|
| Cosmedia ®Guar C 261 | 0.5 |
| Preservative | q.s. |
| Dyes | q.s. |
| Perfume oil | q.s. |
| Water | ad 100.0 |

[24]Polyol fatty acid ester (CTFA name: PEG-7-Glycerylcocoate) (HENKEL)

| 9. Shampoo | |
|---|---|
| Plantaren ®1200 | 4.0 |
| Texapon ®N 70 | 4.0 |
| Texapon ®SB3 | 2.0 |
| Nutrilan ®I | 2.0 |
| Euperlan ®PK-789[25] | 3.0 |
| Zinc stearate | 0.5 |
| Celquat ®H 100[26] | 0.3 |
| Preservative | q.s. |
| Perfume oil | q.s. |
| Dye | q.s. |
| Water | ad 100.0 |

[25]Pearlescer concentrate (CTFA name: Sodiumlaureth Sulfate (and) Glycol Distearate (and) Cocoamide MEA) (HENKEL)
[26]Quaternized cellulose derivative (NATIONAL STARCH)

| 10. Shampoo | |
|---|---|
| Plantaren ®1200 | 4.0 |
| Texapon ®N 70 | 4.0 |
| Texapon ®SB3 | 2.0 |
| Nutrilan ®I | 2.0 |
| Euperlan ®PK-789 | 3.0 |
| Aluminium stearate | 0.5 |
| Celquat ®H 100 | 0.3 |
| Preservative | g.s. |
| Perfume oil | g.s. |
| Dye | q.s. |
| Water | ad 100.0 |

What is claimed is:

1. A process of treating washed hair to provide said hair with improved combability, comprising contacting said hair with a water-based composition comprising:
   (a) from 0.1 to 3% by weight of a zwitterionic polymer,
   (b) from 0.01 to 10% by weight of an alkyl polyglycoside corresponding to formula (I):

$$RO-(Z)_x \quad (I)$$

in which
   R is an alkyl radical containing 6 to 22 carbon atoms,
   Z is a mono- or oligosaccharide,
   x is a number of 1.1 to 5,
or adducts thereof with 1 to 10 moles of ethylene oxide or propylene oxide,
   (c) from 0.5 to 20% by weight of a fatty alcohol; and
   (d) the balance, water.

2. The process of claim 1 wherein (a) is a zwitterionic polymer or polymers comprising a monomer or monomers selected from the group consisting of:
   (a) monomers containing quaternary ammonium groups of the formula (II):

$$R^1-CH=CR^2-CO-X-(C_nH_{2n})-N^{(+)}R^3R^4R^5\ A^{(-)} \quad (II)$$

in which $R^1$ and $R^2$ independently are hydrogen or methyl, $R^3$, $R^4$, and $R^5$ independently are C1 to C4 alkyl, X is NH or O, n is an integer of 2 to 5, and $A^{(-)}$ is an anion of an organic or inorganic acid; and
   (b) monomeric carboxylic acids of the formula (III):

$$R^6-CH=CR^7-COOH \quad (III)$$

in which $R^6$ and $R^7$ independently are hydrogen or methyl.

3. The process of claim 1, wherein Z is glucose and x is a number from 1.1 to 1.6.

4. The process of claim 1, wherein the water-based composition comprises 0.1% to 0.9% by weight of component (b).

5. The process of claim 1, wherein the water-based composition is free of anionic or cationic surfactants.

6. The process of claim 1, wherein the water-based composition is in the form of a lotion, emulsion, or microemulsion comprising 50% to 90% by weight water.

7. The process of claim 1, wherein the water-based composition further comprises a thickening agent or agents selected from the group consisting of ethoxylated fatty alcohols and esters derived from ethoxylated polyols and fatty acids.

* * * * *